US012642839B2

(12) United States Patent 
Billon et al.

(10) Patent No.: US 12,642,839 B2 
(45) Date of Patent: Jun. 2, 2026

(54) MUCOADHESIVE MICROGEL COMPOSITIONS AND METHODS FOR USING THE SAME

(71) Applicants: THE BOARD OF TRUSTEES OF THE LELAND STANFORD JUNIOR UNIVERSITY, Stanford, CA (US); UNIVERSITÉ DE PAU ET DES PAYS DE L'ADOUR, Pau (FR); Centre National de la Recherche Scientifique, Paris (FR)

(72) Inventors: Laurent Billon, St. Faust (FR); Eva Dieuzy, Seyssinet-Pariset (FR); Garbine Aguirre, Lons (FR); Solange Massa, Palo Alto, CA (US); Peter Luke Santa Maria, Redwood City, CA (US)

(73) Assignees: THE BOARD OF TRUSTEES OF THE LELAND STANFORD JUNIOR UNIVERSITY, Stanford, CA (US); UNIVERSITÉ DE PAU ET DES PAYS DE L'ADOUR, Pau (FR); Centre National de la Recherche Scientifique, Paris (FR)

( * ) Notice: Subject to any disclaimer, the term of this patent is extended or adjusted under 35 U.S.C. 154(b) by 818 days.

(21) Appl. No.: 17/615,416

(22) PCT Filed: May 29, 2020

(86) PCT No.: PCT/US2020/035378 
§ 371 (c)(1), 
(2) Date: Nov. 30, 2021

(87) PCT Pub. No.: WO2020/243607 
PCT Pub. Date: Dec. 3, 2020

(65) Prior Publication Data

US 2022/0226436 A1     Jul. 21, 2022

Related U.S. Application Data

(60) Provisional application No. 62/855,687, filed on May 31, 2019.

(51) Int. Cl. 
| | |
|---|---|
| *A61K 38/18* | (2006.01) |
| *A61K 9/06* | (2006.01) |
| *A61K 47/10* | (2017.01) |
| *A61K 47/32* | (2006.01) |

(52) U.S. Cl. 
CPC ............ *A61K 38/1808* (2013.01); *A61K 9/06* (2013.01); *A61K 47/10* (2013.01); *A61K 47/32* (2013.01)

(58) Field of Classification Search 
CPC ...... A61K 38/1808; A61K 9/06; A61K 47/10; A61K 47/32 
See application file for complete search history.

(56) References Cited

U.S. PATENT DOCUMENTS

| | | | |
|---|---|---|---|
| 2017/0190844 A1 | 7/2017 | Zeng et al. | |
| 2017/0232065 A1* | 8/2017 | Santa Maria | ........ A61K 9/0019 514/9.4 |
| 2020/0197266 A1* | 6/2020 | Alard | ...................... A61Q 1/12 |

FOREIGN PATENT DOCUMENTS

| | | |
|---|---|---|
| WO | 2011/084710 A1 | 7/2011 |
| WO | 2013/191759 A1 | 12/2013 |
| WO | 2019/036378 A1 | 2/2019 |

OTHER PUBLICATIONS

Lih et al., "Rapidly curable chitosan-PEG hydrogels as tissue adhesives for hemostasis and wound healing", Biomaterialia, 2012, 8:3261-3269. 
International Search Report and Written Opinion dated Sep. 21, 2020 issued in PCT Application No. PCT/US2020/035378.

* cited by examiner

*Primary Examiner* — Robert A Wax 
*Assistant Examiner* — Olga V. Tcherkasskaya 
(74) *Attorney, Agent, or Firm* — ArentFox Schiff LLP

(57) ABSTRACT

Mucoadhesive microgel compositions, which include an active agent (such as HB-EGF), are provided. Aspects of the invention include a microgel comprising a crosslinked poly (ethylene glycol) methyl ether methacrylate polymer comprising a mucoadhesive functionality. Also provided are methods of making and using the mucoadhesive microgel compositions, e.g., in therapeutic applications. In one embodiment, HB-EGF loaded mucoadhesive microgel compositions are provided, e.g., for prevention or treatment of mucositis conditions, such as therapy induced oral mucositis conditions.

15 Claims, 10 Drawing Sheets

Synthesis of dopamine acrylamide (DA)

- For the synthesis of DA the protocol described by Patil *et al.* was followed with some modifications Amidation reaction Dopamine hydrochloride Acryloyl chloride Dopamine acrylamide (DA)

*Extracted with ethyl acetate and precipitated with hexane*

Synthesis of microgels using DA comonomer

FIG. 5 (CON'T)
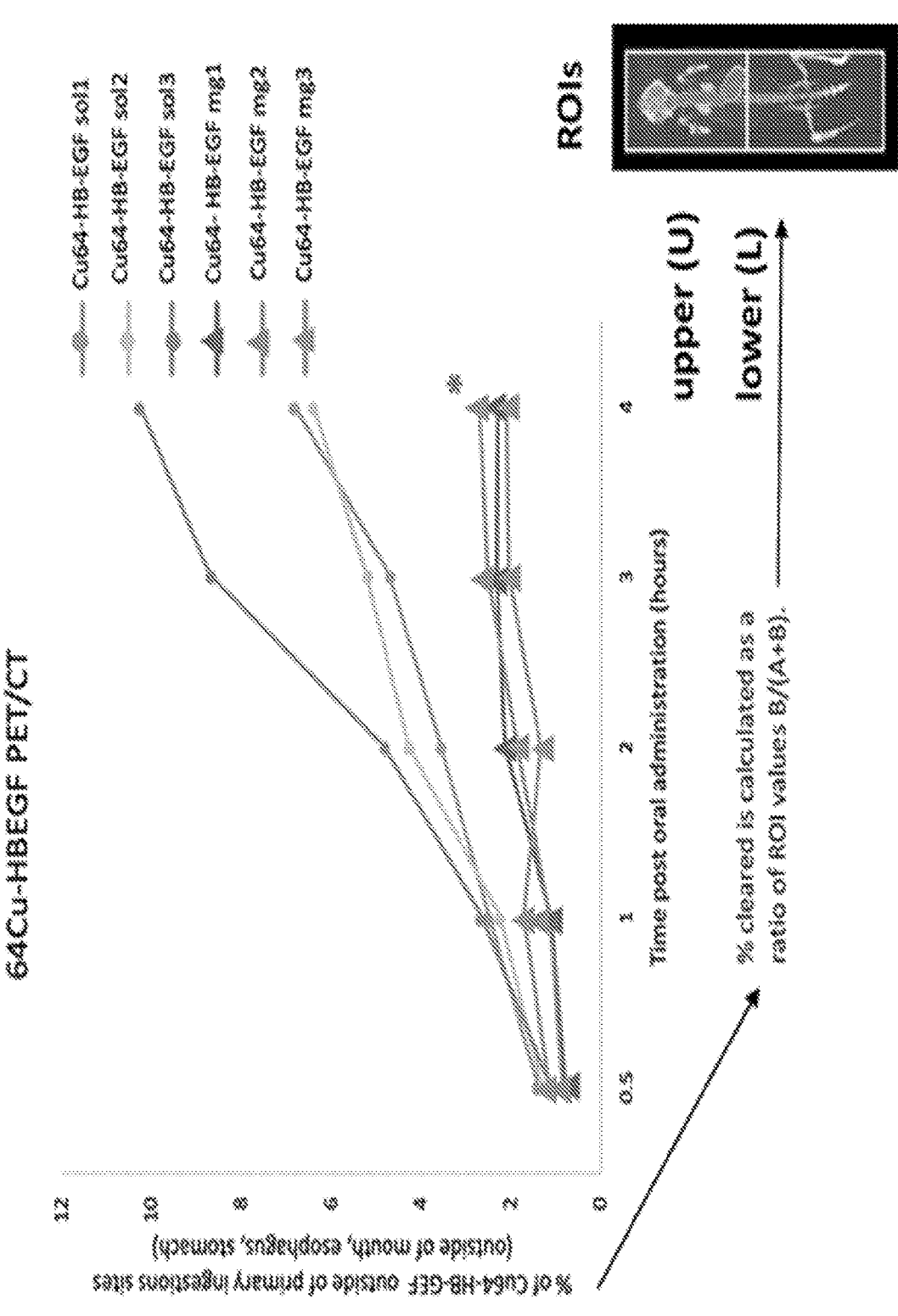

MUCOADHESIVE MICROGEL COMPOSITIONS AND METHODS FOR USING THE SAME

CROSS-REFERENCE TO RELATED APPLICATIONS

This application is a National Phase of PCT/US2020/035378, filed on May 29, 2020, which claims priority to U.S. Provisional Patent Application Ser. No. 62/855,687 filed May 31, 2019; the disclosures of which are herein incorporated by reference in their entireties.

INTRODUCTION

The following discussion of the background art is intended to facilitate an understanding of the present invention only. The discussion is not an acknowledgement or admission that any of the material referred to is or was part of the common general knowledge as of the priority date of the application.

Oral mucositis is the painful inflammation and ulceration of the mucous membranes (oral mucosa) lining the oral cavity, and is caused by injury to the epithelial cells of the oral mucosa which often results from treatment with chemotherapeutic agents or radiation, and the accompanying inhibitory effect on the division and renewal of those epithelial cells. Mucositis most often affects the nonkeratinized mucosa of the cheeks, soft palate, ventral surface of the tongue and floor of the mouth. The development of radio-therapy- or chemotherapy associated oral mucositis depends on the intensity of the chemotherapy treatment, the specific chemotherapy agent(s) involved, the frequency and intensity of radiation treatment, whether or not radiation treatment is concurrent with chemotherapy, the potential use of radio-sensitizing agents, and the tumor type and site. Oral mucositis ranges from mild erythema that causes mucosal discomfort to deep, severe mouth ulcers, and occurs during chemotherapy and/or radiation therapy in approximately 80% of patients with head and neck cancer as well as in approximately 40% of patients with non-head and neck cancer, often limiting the frequency of radiation and/or the radiation exposure that would be optimal for a particular patient (Georgiou et al., "Oral Mucositis: understanding the pathology and management," Hippokratia. (2012)16(3): 215-6; Scully et al., "Oral mucositis: a challenging complication of radiotherapy, chemotherapy, and radiochemotherapy: part 1, pathogenesis and prophylaxis of mucositis." Head Neck. (2003) 25(12):1057-70; and Treister & Sonis "Mucositis: biology and management," Curr Opin Otolaryngol Head Neck Surg. (2007)15(2):123-9). Annually, there are approximately 400,000 cases of treatment-induced damage to the oral cavity, and the damage occurs in many cases almost immediately following the administration of chemotherapy, radiotherapy, or a combination of both. These modalities are used to treat cancers such as leukemia, breast cancer, head and neck cancer, as an adjuvant to cancer removal or for bone marrow transplants (Georgiou et al.)

In patients who receive several rounds of chemotherapy, radiotherapy, or a combination of both, the development of oral mucositis is usually recurring. Serious consequences include severe pain, serious infections, inadequate nutrition, and prolonged hospitalization. At present, there is no effective treatment for oral mucositis, and the current limited treatment options are comprised of oral care, analgesic and anti-inflammatory agents, e.g. Benzydamine, cryotherapy, e.g. swallowing ice chips immediately before radiotherapy, and treatment of secondary infections that may originate from the dynamic bacterial flora within the oral cavity (Worthington et al., "Interventions for preventing oral mucositis for patients with cancer receiving treatment," Cochrane Database Syst Rev. (2006)19(2):CD000978). Keratinocyte Growth Factor (KGF) (Palifermin/Kepivance, Amgen) is a treatment alternative, but it has poor efficacy outside hematological malignancies and must be administered systemically (Elting et al. "Economic impact of palifermin on the costs of hospitalization for autologous hematopoietic stem-cell transplant: analysis of phase 3 trial results," Biol Blood Marrow Transplant. (2007)13(7):806-13). Although topical treatments for oral mucositis exist and provide some relief, they only reduce the burden of symptoms, but neither reduce the occurrence of the problem nor heal the mucosal epithelial cells.

SUMMARY

Mucoadhesive microgel compositions, which include an active agent (such as Heparin Binding Epidermal Growth Factor (HB-EGF)), are provided. Aspects of the invention include a microgel comprising a crosslinked poly (ethylene glycol) methyl ether methacrylate polymer comprising a mucoadhesive functionality. Also provided are methods of making and using the mucoadhesive microgel compositions, e.g., in therapeutic applications. In one embodiment, HB-EGF loaded mucoadhesive microgel compositions are provided, e.g., for prevention or treatment of mucositis conditions, such as therapy induced oral mucositis conditions.

BRIEF DESCRIPTION OF THE FIGURES

FIGS. 1B and 10 provide the structures of reagents used in production of mucoadhesive microgels in accordance with embodiments of the invention.

DEFINITIONS

Figure 1A:
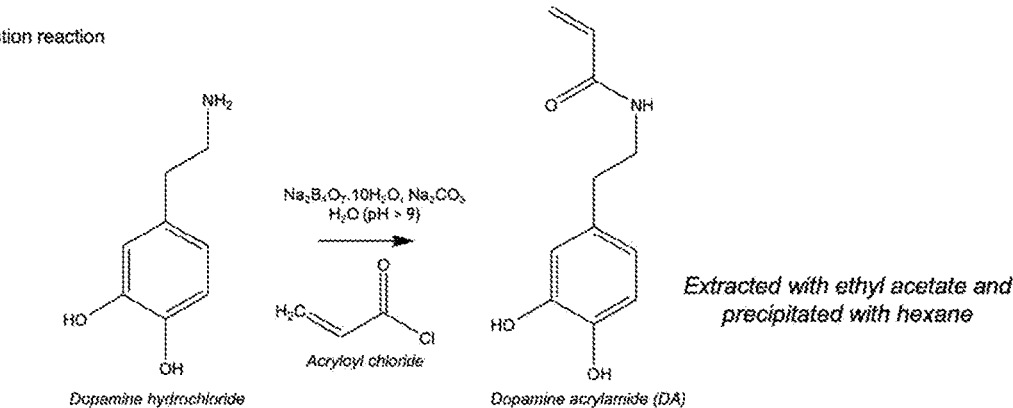
FIG. 1A provides a synthesis scheme for the production of dopamine acrylamide.

A "wound" is a break or discontinuity in the structure of an organ or tissue, including epithelium, connective tissue, and muscle tissue. Examples of wounds include, but are not limited to, wounds, bruises, ulcers, bedsores, grazes, tears, cuts, punctures, psoriasis wounds, tympanic membrane perforations, corneal abrasions and disruptions and burns. A wound may be produced by radiotherapy or chemotherapy. This wound may take the form of an ulcer or mucositis or inflammation that disrupts the epithelium. "Topical" application refers to non-systemic local administration of an active ingredient, and includes application of the composition in question to to mucous membranes, particularly to mucous membranes inside the oral cavity, e.g., within the mouth of a subject.

The term "subject" includes both vertebrates and invertebrates, including, without limitation, mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like. In embodiments, the term "subject" (alternatively referred to herein as "patient") as used herein refers to an animal, such as a mammal, including a human, who has been the object of treatment, observation or experiment.

"Treatment" of a subject or "treating" a subject for a disease or condition herein means reducing or alleviating clinical symptoms of the disease or condition such as impaired or slow wound-healing.

"Promote," "enhance," or "improve" healing after, during or before chemotherapy or radiotherapy, or a combination of both, generally means increasing the speed by which a wound within the oral cavity heals or reducing the severity of the oral mucositis wound or necrotic tissue during or after healing of the wound.

The phrase "therapeutically active agent", which is interchangeably referred to herein as "drug" or "active agent", describes a compound which exhibits a beneficial pharmacological effect when administered to a subject and hence can be used in the treatment of a condition that benefits from this pharmacological effect. An "effective amount" or a "therapeutically effective amount" means an amount of therapeutically active agent that provides a desired therapeutic effect. A therapeutically effective amount can ameliorate, i.e., improve, or present a clinically significant response in a subject. Alternatively, a therapeutically effective amount is sufficient to improve a clinically significant condition in the host.

"Epithelium" refers to the covering of internal and external surfaces of the body, including the lining of vessels and other small cavities. It consists of cells joined by small amounts of cementing substances. Epithelium is classified into types on the basis of the number of layers deep and the shape of the superficial cells. In this context it refers to the superficial layer of cells covering the oral cavity including the esophagus and oropharynx.

As used herein, the term "oral mucosa" means the buccal mucosa, the alveolar mucosa, the floor of the mouth, the tongue, particularly the dorsal and ventral surfaces of the tongue, the hard and soft palate, the uvula, the palatoglossus and palatopharyngeaus muscles, posterior-oropharynx including posterior pharyngeal wall, hypopharynx, and the upper esophagus.

As used herein, "about" or "approximately" mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not.

"Statistically significant" difference means a significance is determined at a confidence interval of at least 90%, more preferably at a 95% confidence interval.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

DETAILED DESCRIPTION

Mucoadhesive microgel compositions, which include an active agent (such as HB-EGF), are provided. Aspects of the invention include a microgel comprising a crosslinked poly (ethylene glycol) methyl ether methacrylate polymer comprising a mucoadhesive functionality. Also provided are methods of making and using the mucoadhesive microgel compositions, e.g., in therapeutic applications. In one embodiment, HB-EGF loaded mucoadhesive microgel compositions are provided, e.g., for prevention or treatment of mucositis conditions, such as therapy induced oral mucositis conditions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

The practice of the present invention will employ, unless otherwise indicated, conventional methods of medicine, pharmacology, chemistry, biochemistry, molecular biology and recombinant DNA techniques, within the skill of the art. Such techniques are explained fully in the literature. See, e.g. K. J. Lee *Essential Otolaryngology: Head and Neck Surgery*, Tenth Edition (McGraw-Hill Education/Medical, 10th edition, 2012); E. N. Myers *Operative Otolaryngology: Head and Neck Surgery: Expert Consult* (Saunders, 2*nd* edition, 2008); A. L. Lehninger, *Biochemistry* (Worth Publishers, Inc., current addition); Sambrook et al., *Molecular Cloning: A Laboratory Manual* (3*rd* Edition, 2001); *Methods In Enzymology* (S. Colowick and N. Kaplan eds., Academic Press, Inc.); and *Pharmaceutical Formulation Development of Peptides and Proteins* (The Taylor & Francis Series in Pharmaceutical Sciences, Lars Hovgaard, Sven Frokjaer, and Marco van de Weert eds., CRC Press; 1*st* edition, 1999).

As summarized above mucoadhesive microgel compositions are provided. In further describing the various aspects of the invention, embodiments of the mucoadhesive microgel compositions are reviewed first in greater detail, followed by review of embodiments of methods of making and using compositions, as well as a review of embodiments of kits that include the compositions.

Mucoadhesive Microgel Compositions

As summarized above mucoadhesive microgel compositions are provided. As the microgel compositions of the invention are mucoadhesive, they are able to adhere to the mucosal layer of a subject, e.g., for an extended period of time, e.g., 0.5 hr or longer, such as 1 hr or longer, 2 hr or longer, 3 hr or longer, 6 hr or longer, etc., by interfacial forces. The mucoadhesive properties of the microgel compositions may be evaluated using any convenient protocol, e.g., in vitro/ex vivo methods, such as methods determining tensile strength, methods determining shear stress, adhesion weight method, fluorescent probe method, flow channel method, mechanical spectroscopic method, falling liquid film method, colloidal gold staining method, viscometer method, thumb method, adhesion number, electrical conductance, swelling properties, in vitro drug release studies, mucoretentability studies, etc. The mucoadhesive properties of the microgel compositions may also be evaluated using in vivo methods, e.g., use of radioisotopes, use of gamma scintigraphy, use of pharmacoscintigraphy, use of electron paramagnetic, resonance(EPR) oximetry, X ray studies, Isolated loop technique (Tangri et. al. "Recent Advances in Oral Mucoadhesive Drug Delivery System: A review," International Jornnal of Pharma. Research and Development (2011) 3(2): 151-162). Methods of evaluating mucoadhesive properties are also described in: Mackie et al., "Innovative Methods and Applications in Mucoadhesion Research," Macromolecular Bioscience (2017) 17(8). The mucoadhesive properties of the microgel compositions may also be evaluated using a BIACORE® integrated chip (IC) mediated protocol, e.g., as described in Kumar et al., "Mucoadhesive Polymers: Means of Improving the Mucoadhesive Properties of Drug Delivery System," J. chem. pharm. Res. (2010) 2(5): 418-32). In such assays, the polymer (powder) is immobilized on to the surface of the IC with the subsequent passage of the mucin solution over the same. This results in the interaction of the mucin with that of the polymer surface. The polymer-mucin interaction is measured by an optical phenomenon called Surface Plasmon Resonance (SPR), which measures the change in the refractive index when mucin binds on the polymer surface. See also Takeuchi et al., "Novel mucoadhesion tests for polymers and polymer-coated particles to design optimal mucoadhesive drug delivery systems," Adv. Drug Deliver. Rev. (2005) 57(11):1583-1594 and Thongborisute & Takeuchi, "Evaluation of mucoadhesiveness of polymers by BIACORE method and mucin-particle method," Int J Pharm. (2008) 354(1-2):204-9. Using Atomic Force Microscopy (AFM) assay, mucoadhesive microgel compositions according to embodiments of the invention exhibit mucoadhesive properties with respect to the surface showing and increased adhesion in the adhesion channel of the described assay. Tensile strength (Instron) results also provide evidence that the microgels in the form of a film increase adhesion between two surfaces of porcine mucosa using human saliva in between the surfaces.

Mucoadhesive cross-linked microgels of the invention include a crosslinked poly(ethylene glycol) methyl ether methacrylate polymer that includes a mucoadhesive functionality. "Microgels", in the sense of the present description, are compositions in the form of an aqueous dispersion of microgel particles or in the form of a film comprising microgel particles, where the microgel particles are crosslinked polymers in the form of a spherical particles having a size that varies, e.g., from 100 nm to 500 nm in the dry state (i.e., containing less than 2% by weight of water), such as between 350 and 450 nm, and in some instances between 375 and 425 nm, e.g., on the order of 400 nm. When present a film, the film can have a thickness that varies, ranging in some instances from 10 to 500 microns, such as from 100 to 400 microns. The microgels of the invention may include only one type of a crosslinked copolymer. The crosslinking density of the copolymer in the microgels may vary within the particle volume generating thereby a "core-shell" structure comprising two parts: one of the two parts having a crosslinking density that is lower than the other part. The crosslinked polymer can have a constant crosslinking rate within the entire volume of the microgel particle. In other instances, crosslinking density can be higher or lower at the surface of the particles.

Microgels in accordance with embodiments of the invention include at least one crosslinked poly(ethylene glycol) methyl ether methacrylate polymer having a mucoadhesive functionality, wherein the crosslinked polymer comprises copolymer chains having diethylene glycol methacrylate monomeric units, oligoethylene glycol methacrylate monomeric units, e.g., comprising from 6 to 10 ethylene glycol moieties, methacrylic acid monomeric units, mucoadhesive monomeric units and crosslink moieties.

According to an embodiment, the crosslinked polymer of the microgel comprises copolymer chains having diethylene glycol methacrylate monomeric units, oligoethylene glycol methacrylate monomeric units, e.g., comprising from 4 to 10 ethylene glycol moieties, methacrylic acid monomeric units and mucoadhesive functionality monomeric units. The monomeric units may be: di(ethylene glycol) methyl ether methacrylate; oligo(ethylene glycol) methyl ether methacrylate having from 7 to 9 ethylene glycol moieties; and methacrylic acid. Oligo(ethylene glycol) methyl ether methacrylate monomeric units can also have from 8 to 9 ethylene glycol moieties.

The mucoadhesive functionality monomeric units may be derived from mucoadhesive functionality bearing monomers. Such monomers may include a variety of different mucoadhesive functionalities, such as but not limited to: dopamine, thiolated polymers (thiomers), lectins, and the like. In some instances, the mucoadhesive functionality monomer is dopamine acrylamide.

The copolymer chains can be linked with a crosslink deriving from any convenient crosslinking agent. A "crosslink" is a moiety (part of a molecule) that links the copolymer chains together. This crosslink derives from a "crosslinker" molecule or crosslinking agent that is mixed with the monomers during the polymerization process of the crosslinked polymer. Examples of suitable crosslinking agents that may be employed include, but are not limited to: oligo(ethylene glycol) diacrylate comprising from 1 to 10, such as 4 to 5, ethylene glycol units, 1,3-butanediol diacrylate, 1,4-butanediol diacrylate, 1,6 hexanediol diacrylate, pentaerythritol diacrylate monostearate, glycerol 1,3-diglycerolate diacrylate, neopentyl glycol diacrylate, poly(propylene glycol) diacrylate, 1,6-hexanediol ethoxylate diacrylate, trimethylolpropane benzoate diacrylate, ethylene glycol dimethacrylate, 1,3-butanediol dimethacrylate, 1,4-butanediol dimethacrylate, 1,6-hexanediol dimethacrylate, glycerol dimethacrylate, N,N-divinylbenzene, N,N'-methylenebisacrylamide, N,N-(1,2-dihydroxyethylene)bisacrylamide, poly(ethylene glycol) diacrylamide, allyl disulfide, bis(2-methacryloyl)oxyethyl disulfide and N,N-bis(acryloyl)cystamine. According to one embodiment, the crosslinker has di(meth)acrylate end groups and a moiety selected in the group consisting of —$(CH_2$—$CH_2$-$0)_n$—$CH_2$—$CH_2$— where n is from 0 to 6, —NH—$CH_2$—NH— and mixtures thereof. The crosslinking agent is for example N,N'-methylenebisacrylamide, ethylene glycol)dimethacrylate, or oligo(ethylene glycol) diacrylate. In some instances, the crosslinking agent represents for example from 1 to 5 mol. % of the total number of moles of the three monomeric units.

In some instances, a crosslinked polymer comprises diethylene glycol methacrylate monomeric units, oligoethylene glycol methacrylate monomeric units comprising from 8 to 9 ethylene glycol moieties, and a linker comprising di(meth)acrylate end groups and a moiety selected in the group consisting of —$CH_2$—$CH_2$—, —$(CH_2$—$CH_2$-$0)_n$-$CH_2$—$CH_2$— where n is from 4 to 5, and —NH—$CH_2$—NH—. Inner structure of the microgels can depend on the crosslinker used. For example, active substances having a molecular weight that is lower than 1000 g/mol can be encapsulated into copolymer having —NH—$CH_2$—NH— bridges, active substances having a molecular weight that is between 1,000 and 4,000 g/mol can be encapsulated into copolymer having —$CH_2$—$CH_2$— bridges, and active substances having a molecular weight being from 4,000 to 10,000 g/mol can be encapsulated into copolymer having —$(CH_2$—$CH_2$-$0)_n$-$CH_2$—$CH_2$— where n is from 4 to 5 bridges.

According to one embodiment, the microgels of the invention can be obtained by aqueous phase precipitation polymerization of the following monomers:

di(ethylene glycol) methyl ether methacrylate, an oligo(ethylene glycol) methyl ether methacrylate comprising from 6 to 10 ethylene glycol moieties, such as from 7 to 9 ethylene glycol moieties, and including from 8 to 9 ethylene glycol moieties, a (meth)acrylic acid monomer, and a mucoadhesive functionality bearing comonomer, in the presence of a crosslinking agent.

In the initial monomer mixture, di(ethylene glycol) methyl ether methacrylate may be present for example 50 mol % to 90 mol % of the total number of moles of the monomers, oligo(ethylene glycol) methyl ether methacrylate preferably may be present 5 to 50 mol % of the total number of moles of the monomers the (meth)acrylic acid monomer preferably may be present from 0.1 mol % to 20 mol %, for example ranging from 0.1 to 5 mol %, of the total number of moles of the monomers, and the mucoadhesive functionality bearing comonomer, e.g., dopamine acrylamide, may be present may be present from 0.1 mol % to 20 mol %, for example ranging from 0.1 to 5 mol %, of the total number of moles of the monomers, the sum of these contents being equal to 100%. The molar ratio (a:b) between di(ethylene glycol) methyl ether methacrylate (a) and oligo(ethylene glycol) methyl ether methacrylate (b) may vary, and in some instances ranges between 1:1 and 20:1, for example between 5:1 and 10:1. Within the meaning of the invention the expression "between" excludes the numerical limits that succeed it. On the other hand, the expression "ranging from . . . to" includes the stated limits.

The monomer di(ethylene glycol) methyl ether methacrylate that is used to prepare the crosslinked polymer of the invention represents for example 80 to 90 mol % of the total number of moles of the three monomers, the oligo(ethylene glycol) methyl ether methacrylate monomer preferably represents 5 to 15 mol % of the total number of moles of the monomers and methacrylic add preferably represents 0.1 to 10 mol % of the total number of moles of the monomers, the sum of these three contents being equal to 100%. The (meth)acrylic add monomer can have the formula $$CR_1R_2 = CR_3R_4$$

in which $R_1$, $R_2$, $R_3$ and $R_4$ represent a hydrogen, a halogen or a hydrocarbon group, at least one of the four groups comprising a —COOH or —COO-M⁺ group, M⁺ representing a cation. The (meth)acrylic add monomer can be selected from the group consisting of methyl acrylic, methyl methacrylic, ethyl acrylic, ethyl methacrylic, n-butyl acrylic, and n-butyl methacrylic, methacrylic, itaconic or acrylic adds. Methacrylic add is present in some instances.

In one embodiment, the molar fraction of diethylene glycol methacrylate monomeric units is from 80 mol. % to 90 mol. %, such as from 82 mol. % to 86 mol. %, the molar fraction of oligoethylene glycol methacrylate monomeric units is from 5 mol. % to 15 mol. %, such as from 7 mol. % to 11 mol. %, the molar fraction of (meth)acrylic add monomeric units is from 2 mol. % to 8 mol. %, such as from 3 mol. % to 7 mol. %, the molar fraction of mucoadhesive bearing monomeric units, e.g., dopamine acrylamide monomeric units, is from 2 mol. % to 8 mol %, such as from 3 mol. % to 7 mol. %, and the molar fraction of the crosslink is from 1 to 3 mol. %, molar fractions being the molar fractions in the crosslinked polymer.

Mucoadhesive microgels as described herein are loaded with one or more active agents.

Further details regarding microgels and fabrication thereof that may be adapted by incorporating a mucoadhesive functionality bearing monomer component to produce mucoadhesive microgels in accordance with embodiments of the invention are described in published POT Application Publication Nos. WO/2016/110615 and WO/2019/077404, as well as U.S. Pat. No. 10,287,403; the disclosures of which are herein incorporated by reference.

Active-Agent Loaded Mucoadhesive Microgels

The mucoadhesive microgels are loaded with an active agent. By "loaded" is meant that the microgel particles include an amount of an active agent(s). As such, an amount of active agent is present in the microgel particle, and may be viewed as entrapped in the microgel particle. The term "entrap" means that the active agent is located within the polymer network of the microgel. The network of the crosslinked polymer can form a barrier around the molecule that can be suppressed by some physical change in the network, for example with a pH variation trigger, a temperature variation trigger, or a solvent variation trigger. The entrapped organic molecule may not be linked to the crosslinked polymer with a covalent bond. The entrapped active agent can have electrostatic interactions, Van der Walls bonds or hydrogen bonds with the crosslinked polymer, that can be engaged between C=C bonds of —OH groups of the organic molecules and ethylene glycol moieties of the crosslinked polymer. While the amount of active agent loaded into the microgel particles may vary, in some instances the weight ratio of active agent to crosslinked polymer in the microgel is from 250 microgram/mg to 10 mg/mg. In some instances, the weight ratio of active substance to crosslinked polymer is lower than 10 mg/mg and higher than a lower limit selected in the group consisting of 250 microgram/mg, 350 microgram/mg, 400 microgram/mg, 450 microgram/mg, 500 microgram/mg, 550 microgram/mg, 600 microgram/mg, 650 microgram/mg, 700 microgram/mg, 750 microgram/mg, 800 microgram/mg, 850 microgram/mg, 900 microgram/mg and 1 mg/mg. According to one embodiment, the weight ratio of active substance to crosslinked polymer is higher than 550 microgram/mg.

A variety of different active agents may be loaded into the microgel particles. In some instances, the active agent is a small molecule. Naturally occurring or synthetic small molecule compounds of interest include numerous chemical classes, such as organic molecules, e.g., small organic compounds having a molecular weight of more than 50 and less than about 2,500 daltons. The compounds can include functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Small molecules of interest include, but are not limited to, acne reducing drugs, antibiotics, antivirals, antifungals, antineoplastics, antiangiogenics, antiarrhythmics, antiparkinson drugs, anticoagulants, anticonvulsants, anticancer drugs, antiallergic drugs, antidepressants, antidiabetic drugs, antihistamines, antihypertensives, antimigraine drugs, antipsychotics, anxiolytics, sedatives, hypnotics, bile add sequestrants, bisphosphonates, bone resorption inhibitors, bronchodilators, lipid-lowering drugs, cardiovascular drugs, central nervous system drugs, chelating agents, cholesterol absorption inhibitors, contraceptives, decongestants, dermatological agents, diagnostic agents, radiopharmaceuticals, diuretics, expectorants, drugs used in treating alcohol, tobacco and illegal drug dependence, fibric add drugs, gastrointestinal drugs, general anesthetics, growth hormones, heparins, heparin antagonists, herbal products, immunologic agents, immunosuppressants, inotropic agents, interferons, mast cell stabilizers, mouth, nose and throat drugs, muscle relaxants, nutritional products, ophthalmic drugs, antibiotic drugs, probiotics, psychotherapeutic drugs, radiological agents, respiratory drugs, sex hormones, spermicidal agents, statins, thrombolytics, thyroid drugs, vaginal preparations, vitamins and the like.

In some instances the active agent is a nucleic add active agent. Nucleic add active agents may vary and include, but are not limited to, nucleic adds encoding polypeptides of interest, which nucleic adds may be present in a vector. Various vectors (e.g., viral vectors, bacterial vectors, or vectors capable of replication in eukaryotic and prokaryotic hosts) can be used in accordance with the present invention. Numerous vectors which can replicate in eukaryotic and prokaryotic hosts are known in the art and are commercially available. In some instances, such vectors used in accordance with the invention are composed of a bacterial origin of replication and a eukaryotic promoter operably linked to a DNA of interest. Also of interest are nucleic acid inhibitory agents, e.g., DNA, RNA (e.g., RNAi agents), chimeric RNA/DNA, protein nucleic acid, and other nucleic acid derivatives In some instances, the active agent is a peptide or polypeptide active agent. Polypeptides active agents are polypeptides that, upon administration to a subject, exhibit a desired activity. The term "polypeptide" as used herein refers to full-length proteins as well as portions or fragments thereof which exhibit the desired activity. Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses a TIMP protein. Polypeptides of interest may vary in terms of amino acid sequence length and molecular weight. In some instances, the polypeptides range in length from 175 to 350, such as from 200 to 250 and including from about 200 to 225 amino acid residues. Polypeptides as described herein may be obtained from naturally sources, e.g., via purification techniques, chemically synthesized or produced using recombinant protocols, as desired.

The terms "peptide," "oligopeptide" and "polypeptide" refer to any compound comprising naturally occurring or synthetic amino acid polymers or amino acid-like molecules including but not limited to compounds comprising amino and/or imino molecules. No particular size is implied by use of the terms "peptide," "oligopeptide" or "polypeptide" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and U.S. Pat. No. 5,977,301; Nguyen et al. (2000) Chem Biol. 7(7):463-473; and Simon et al. (1992) Proc. Natl. Acad. Sci. USA 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this invention can have a maximum length suitable for the intended application. Preferably, the polypeptide is between about 3 and 100 residues in length. Generally, one skilled in art can easily select the maximum length in view of the teachings herein. Further, peptides and polypeptides, as described herein, for example synthetic peptides, may include additional molecules such as labels or other chemical moieties.

Thus, references to polypeptides or peptides also include derivatives of the amino acid sequences of the invention including one or more non-naturally occurring amino acids. A first polypeptide or peptide is "derived from" a second polypeptide or peptide if it is (i) encoded by a first polynucleotide derived from a second polynucleotide encoding the second polypeptide or peptide, or (ii) displays sequence identity to the second polypeptide or peptide as described herein. Sequence (or percent) identity can be determined as described below. Preferably, derivatives exhibit at least about 50% percent identity, more preferably at least about 80%, and even more preferably between about 85% and 99% (or any value therebetween) to the sequence from which they were derived. Such derivatives can include postexpression modifications of the polypeptide or peptide, for example, glycosylation, acetylation, phosphorylation, and the like.

Amino acid derivatives can also include modifications to the native sequence, such as deletions, additions and substitutions (generally conservative in nature), so long as the polypeptide or peptide maintains the desired activity (e.g., promote epithelial cell proliferation and wound healing). These modifications may be deliberate, as through site-directed mutagenesis, or may be accidental, such as through mutations of hosts that produce the proteins or errors due to Polymerase Chain Reaction (PCR) amplification.

By "fragment" is intended a molecule consisting of only a part of the intact full length sequence and structure. The fragment can include a C-terminal deletion an N-terminal deletion, and/or an internal deletion of the polypeptide. Active fragments of a particular protein or polypeptide will generally include at least about 5-14 contiguous amino acid residues of the full length molecule, but may include at least about 15-25 contiguous amino acid residues of the full length molecule, and can include at least about 20-50, 60-90, or more contiguous amino acid residues of the full length molecule, or any integer between 5 amino acids and the full length sequence, provided that the fragment in question retains biological activity, such as HB-EGF activity, as defined herein (e.g., the ability to bind to and activate an Epidermal Growth Factor (EGF) receptor and promote epithelial cell proliferation and/or wound healing).

As such, therapeutically active agents include hormones, receptors, cytokines, hematopoietic factors, growth factors, anti-obesity factors, trophic factors, anti-inflammatory factors, proteins, polypeptides, antibodies, enzymes and the like. Polypeptide/protein active agents of interest include, but are not limited to, oxytocin, vasopressin, adrenocorticotropic hormone, epidermal growth factor, platelet- derived growth factor, heparin binding epidermal growth factor, prolactin, luliberin, growth hormone, growth hormone releasing factor, insulin, somatostatin, glucagon, interleukin-2, interferon-alpha, interferon-beta, interferon-gamma, gastrin, tetragastrin, pentagastrin, urogastrone, secretin, calcitonin, enkephalins, endorphins, angiotensins, thyrotropin releasing hormone, tumor necrosis factor, nerve growth factor, granulocyte-colony stimulating factor, granulocyte macrophage-colony stimulating factor, macrophage-colony stimulating factor, heparinase, bone morphogenic protein, human Atrial Natriuretic Peptide (hANP), glucagon-like peptide, interleukin-11, renin, bradykinin, bacitracins, polymyxins, colistins, tyrocidine, gramicidins, cyclosporine, enzymes, cytokines, monoclonal antibodies, vaccines and the like.

Active agent loaded mucoadhesive microgels of the invention can be prepared according to the steps of:

preparing a dispersion of unloaded microgel particles in water, preparing a solution of the active agent, mixing the dispersion and the solution causing encapsulation of the active agent in the microgel particles, and recovering active agent loaded microgel particles.

Unloaded microgel particles are prepared for example by a precipitation polymerization method comprising a step of contacting in an aqueous phase, in the presence of a cross-linking agent, the monomers described above, at a temperature of between 40° C. and 90° C., such as of the order of 70° C. The process of the invention does not require the presence of a surfactant such as SOS (dodecyl sulfate sodium), and polymerization may be initiated by addition of a water-soluble radical initiator, for example potassium persulfate (KPS).

Active agent molecules can be encapsulated into microgels that are in the form of an aqueous dispersion, or into microgels that have been prepared in the form of a film according to the description above, in a prior step. Mixing step of active substance solution and unloaded microgel dispersion preferably comprises a step of heating at a temperature that is higher than the volume phase transition temperature of the unloaded microgel particles, and a step of cooling the obtained dispersion of loaded microgels at ambient temperature (25° C.).

The feeding solution of the active agent can be obtained by dissolution of a determined amount of the active substance in an appropriate solvent such as water or a solvent that is miscible with water, such as alcohols. Alcohols can be ethanol, propylene glycol, butylene glycol. Other solvents such as isododecane, isohexadecane, or decamethylcyclopentasiloxane can also be used. A polar solvent that is soluble or miscible with water may be particularly advantageous-to enhance the loading amount of the active substance into the microgels. Complete dissolution of a determined amount of the active substance in the solvent can be performed at a temperature being from ambient temperature to a temperature that is above the volume phase transition temperature of the unloaded microgel particles.

In a particular embodiment, a dispersion of unloaded microgel particles in water (0.1 to 10 mg particles/mL water) is heated at a process temperature. A solution of active agent in a solvent (0.5-125 mM or 0.5-2.5 mM) is heated at this process temperature as well, and then mixed with the unloaded microgel particle aqueous dispersion under stirring while maintaining the same temperature. The process temperature can be a temperature that is higher or lower that the volume phase transition temperature (VPTT) of unloaded microgel particles, the particles being respectively in collapse or swollen state. For example, the process temperature is 10° C. or higher, such as 15° C. or higher, than the VPTT, or at 10° C. or lower, such as 15° C. or lower than the VPTT. Removal of the solvent and removal of active substance molecules that have not been trapped into the microgel particles can be performed subsequently, in order to obtain microgels according to the invention. Removal of active molecules that have not been entrapped can be performed by filtering and/or by centrifugation.

In embodiments, the mucoadhesive microgels exhibit high entrapment efficiency for active agents. The Entrapment efficiency (EE %) is defined as the ratio of the weight of the active agent that is entrapped in the loaded microgels and the amount of the active agent that is contained in the feeding solution. The Entrapment efficiency (EE %) can also be defined as the ratio A/B of the entrapped substance amount (A) and the feeding substance amount (B), as defined here above. The "amount of the active agent in the feeding solution"—also called "the feeding active agent amount" in the following description—is the weight of the active agent in the feeding solution (in pg or mg) per 1 mg of unloaded microgel particles that are used to entrap the active substance. The feeding active agent amount unit may be written in a shorter way "mg/mg" or "microgram/mg". Embodiments enable a high entrapment efficiency EE % of the active agent, meaning that a very high proportion of the initial amount of active agent that is nixed with unloaded microgel particles (in the form of a aqueous dispersion of microgel particles, or in the form of a film of assembled microgel particles) is successfully entrapped within the microgel particles. In some instances, EE % is higher than a upper limit selected in the group of 50%, 60%, 70%, 80%, 90%, 95% when the amount of the active agent in the feeding substance is from 500 microgram/0 mg unloaded microgels) to 10 mg/(1 mg unloaded microgels). In some instances, the Entrapment efficiency (EE %) ranges from a lower limit selected in the group consisting of 50%, 55%, 60%, 65%, 70%, 75%, 80%, 85%, 90%, 95%, to a upper limit of 100%.

In some instances, active agent loaded mucoadhesive microgels of the invention provide for continuous release of their active agent payload out of the microgels, which release can be observed for 6 hours or longer, such as 12 hours or longer, including 24 hours or longer or even 48 hours or longer. At the end of this period, the release can stop and a maximum total release percentage of the active agent can be lower than 100% and higher than a value selected in the group consisting of 10%, 15%, 20%, 25%, 30%, 35%, 40%, 45%, 50%, 55%, 60%, 65%, 70%, 75%, 80%, 90% and 95%.

Further details regarding microgels and fabrication thereof that may be adapted by incorporating a mucoadhesive functionality bearing monomer component to produce mucoadhesive microgels in accordance with embodiments of the invention are described in published POT Application Publication Nos. WO/2016/110615 and WO/12019/077404, as well as U.S. Pat. No. 10,287,403; the disclosures of which are herein incorporated by reference.

Heparin Binding Epidermal Growth Factor (HB-EGF) Mucoadhesive Microgels

In some embodiments, the active agent that is loaded into mucoadhesive microgels is an HB-EGF active agent. HB-EGF active agents are compounds that exhibit the desired HB-EGF activity. Any form of HB-EGF may be used in the practice of the invention, including the immature proprotein form of HB-EGF and various active forms of HB-EGF produced by proteolytic processing of the proprotein, including membrane-anchored and soluble forms of HB-EGF, as well as biologically active fragments, variants, analogs, and derivatives thereof that retain HB-EGF biological activity (e.g., promote epithelial cell proliferation and wound healing). The HB-EGF for use in the methods of the invention may be native, obtained by recombinant techniques, or produced synthetically, and may be from any source. Representative human HB-EGF sequences are listed in the National Center for Biotechnology Information (NCBI) database, including HB-EGF sequences from a number of different species. See, for example, NCBI entries: Accession Nos: L17032, L1703, NP_001936, NM_001945, NP_037077, NP_990180, NP_001137562, NP_034545, NP_001104696, NP_001093871, XP_003829241, XP_005425426, NP_001244398, XP_014126447, XP_014131937, XP_013998941, XP_005523504, XP_005617336, XP_005617335, XP_005617334, XP_005617333, XP_848614, XP_013914901, XP_013821061, XP_013809984, XP_005382088, XP_005382087, XP_005503713, XP_005327340, XP_005356014, XP_005238935, XP_013047270, XP_012996694, XP_010869528, XP_005065318, XP_003477196, XP_012956154, XP_004841917, XP_004744871, XP_012875794, XP_004696718, XP_004652486, XP_002937773, XP_004610052, XP_004586534, XP_004586533, XP_012697566, XP_003782186, XP_012604548, XP_004686855, XP_012501863, XP_012501862, XP_012501861, XP_004397849, XP_002190931, XP_004280331, XP_003756676, XP_004643289, XP_004477893, XP_003266511, XP_012327017, XP_012006016, XP_012006015, XP_012006014, XP_012006013, XP_004008912, XP_011714646, NP_001158639, NP_001273220; all of which sequences (as entered by the date of filing of this application) are herein incorporated by reference. Any of these sequences, or a biologically active fragment thereof, or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used to produce a composition comprising HB-EGF as described herein. Additionally, the HB-EGF may comprise post-translational modifications, such as glycosylation or phosphorylation. Although any source of HB-EGF can be utilized to practice the invention, preferably the HB-EGF is derived from a human source, particularly when the subject undergoing therapy is human. Additional details regarding HB-EGF active agents and preparation thereof that may be employed in embodiments of the present invention are provided in United States Published Patent Application Nos. 20170232065 and 20180256684; the disclosures of which are herein incorporated by reference.

Pharmaceutical Compositions

Active agent loaded mucoadhesive microgels such as described above may be combined with one or more additional components to produce a pharmaceutical composition suitable for delivery to a subject. The active agent loaded mucoadhesive microgels can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof. Antioxidants are used to prevent oxidation, thereby preventing the deterioration of the active agent (e.g., HB-EGF) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof. Exemplary surfactants include: polysorbates, such as "TWEEN® 20" and "TWEEN® 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as ethylenediaminetetraacetic acid (EDTA); and zinc and other such suitable cations. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of active agent, e.g., HB-EFG, in the pharmaceutical composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The compositions encompass all types of formulations, including liquid pharmaceutical compositions, solutions and suspensions e.g., for oral, topical, or localized delivery. In some instances the composition is a mouth wash or spray formulation.

In some instances the compositions may include one or more additional mucoadhesive components. In such instances, the microgels may be combined with, but not covalently bound to, the one or more additional mucoadhesive polymeric agents. Additional mucoadhesive components of interest include, but are not limited to: mucoadhesive polymeric agents, which may be naturally occurring or synthetic polymeric agents. As such, mucoadhesive polymeric agents include those selected from the group consisting of naturally occurring mucoadhesive polymeric agents, synthetic mucoadhesive polymeric agents and combinations thereof. Naturally occurring agents include, but are not limited to, polysaccharides, e.g., starches, chitosan, heparin, polymers and the like. Non-naturally occurring agents include, but are not limited to pluronics (i.e., poloxamers), polymers, peptides, peptoids and the like. When present, the amount of such additional mucoadhesive polymeric agents may vary, ranging in some instances from 1% to 50% of the total solution.

The compositions herein may optionally include one or more additional active agents, as desired. For example, mucoadhesive compositions, e.g., as described above, may be combined with one or more additional active agents, such as other drugs for treating the oral cavity and oropharynx before, during and/or after chemotherapy or radiotherapy. For example, preparations including HB-EGF and one or more other drugs for treating a post-operative wound, such as, but not limited to, analgesic agents, anesthetic agents, antibiotics, anti-inflammatory agents, substances that increase neoepithelial adherence, or other growth factors, or other agents that promote wound healing, may be prepared and used. Alternatively, such agents can be contained in a separate composition from the composition comprising HB-EGF and co-administered concurrently, before, or after the composition comprising HB-EGF.

Methods

Aspects of the invention further include methods of administering mucoadhesive microgels, such as active agent loaded mucoadhesive microgels (e.g., HB-EGF loaded mucoadhesive microgels) to a subject. In general, methods of the invention include delivery an amount of a mucoadhesive microgel, e.g., as described above, such as in the form of a pharmaceutical composition, to a location of a subject. In some instances the methods include orally administering the composition to a subject in need thereof, e.g., so that the composition and microgel particles therein contact one or more both of the oral cavity and oropharynx. In practicing the methods, at least one therapeutically effective cycle of treatment with a composition will be administered to a subject. A given cycle of treatment may include administration of one or more dosages, where the dosages may be administered according to a prescribed dosage regimen, which may vary, e.g., 1 to 4 times per day, for 1 or more days, e.g., 1 or more weeks, etc.

As described above, in some instances, the active agent is HB-EGF. In some instances, at least one therapeutically effective cycle of treatment with a mucoadhesive microgel composition comprising HB-EGF will be administered to a subject in need thereof, e.g., in need of treatment/prevention for therapy induced, e.g., radiotherapy or chemotherapy-associated, oral mucositis; in need of treatment for treatment/prevention for oral epithelial disease where DNA damage is the underlying cause; in need of treatment/prevention for upper aerodigestive tract mucositis or where DNA damage is the underlying cause; etc. In examples of such embodiments, the methods are methods of modulating oral mucositis in a subject, where by modulating is meant either preventing the occurrence of mucositis or treating mucositis, e.g., by reducing the severity of mucositis, enhancing the recovery from mucositis, etc.

By "therapeutically effective cycle of treatment" is intended a cycle of treatment that, when administered, brings about a positive therapeutic response with respect to treatment of an individual receiving chemotherapy, radiotherapy, or a combination of both. Of interest in some embodiments is a cycle of treatment with a composition comprising HB-EGF that improves wound healing and epithelial regeneration when applied following chemotherapy, radiotherapy, or a combination of both. Improved wound healing and epithelial regeneration may include increasing the speed by which a wound in the oral cavity heals or how quickly the epithelial layer in the oral cavity regenerates, as assessed in relation to the total epithelial area in the oral cavity measured, or how quickly the keratinocytes grow in the oral cavity, as assessed by the thickness of the keratin layer. Improved wound healing and epithelial regeneration may also include decreasing the depth or size of the wound that may develop within the oral cavity, decreasing the number of wounds (mucositis ulcers) that develop, or a lessening the severity of a wound, or reducing the extent of residual scar or keloid or necrotic tissue formation. Additionally, a therapeutically effective dose or amount may reduce or prevent post-operative hemorrhaging.

In certain embodiments, multiple therapeutically effective doses of compositions comprising HB-EGF and/or one or more other therapeutically active agents, such as other growth factors or drugs or agents for treating a wound, or other medications will be administered. The compositions of the present invention are typically, although not necessarily, administered orally, via transepithelial injection, topically, or locally.

Compositions comprising HB-EGF and/or one or more other therapeutically active agents may be administered directly on the surface of a wound within the oral cavity or adjacent to a wound. For example, the composition may be administered by spraying the composition on the wound, as a topical paste. The composition may also be added to wound dressings. Alternatively, the composition may be administered orally as a wash, gargle, or rinse. The particular composition and appropriate method of administration are chosen to target the active agent, e.g., HB-EGF, to the site in need of epithelial regeneration and wound healing.

The pharmaceutical preparation of the composition comprising HB-EGF and/or one or more other therapeutically active agents can be liquid or semi-solid, a solution or suspension, an emulsion, a syrup, a cream, an ointment, a lotion, a patch, a tablet, a capsule, a powder, a gel, a matrix, a suppository, or the like. The pharmaceutical compositions comprising HB-EGF and other agents may be administered using the same or different routes of administration in accordance with any medically acceptable method known in the art.

In another embodiment, the pharmaceutical compositions comprising HB-EGF and/or other agents are administered prophylactically with the intention to prevent or mitigate the development of radiotherapy- or chemotherapy-associated oral mucositis prior to one or more rounds of chemotherapy or radiotherapy, or a combination of both. Such prophylactic uses will be of particular value for subjects who suffer from a condition which impairs or slows down the healing of a wound resulting in the context of radiotherapy- or chemotherapy-associated oral mucositis, and also will be of value for subjects without otherwise impaired wound healing.

In another embodiment, the pharmaceutical compositions comprising HB-EGF and/or other agents are administered concurrently, e.g., at the same time as one or more rounds of chemotherapy or radiotherapy, or a combination of both, are applied to a subject with the intention to prevent or mitigate the development of radiotherapy- or chemotherapy-associated oral mucositis. In some embodiments, the concurrent administration of the pharmaceutical compositions comprising HB-EGF and/or other agents is then followed by one or more administrations of pharmaceutical compositions comprising HB-EGF and/or other agents in accordance with a defined treatment regimen after the chemotherapy or radiotherapy, or a combination of both, is completed.

In another embodiment, the pharmaceutical compositions comprising HB-EGF and/or other agents are administered a) prior to one or more rounds of chemotherapy or radiotherapy, or a combination of both, b) concurrently, e.g., at the same time as one or more rounds of chemotherapy or radiotherapy, or a combination of both, are applied to a subject, and/or c) after the chemotherapy or radiotherapy, or a combination of both, is completed.

In another embodiment, the pharmaceutical compositions comprising HB-EGF and/or other agents are administered a) prior to one or more rounds of chemotherapy or radiotherapy, or a combination of both and b) concurrently, e.g., at the same time as one or more rounds of chemotherapy or radiotherapy, or a combination of both, are applied to a subject.

In another embodiment, the pharmaceutical compositions comprising HB-EGF and/or other agents are administered a) concurrently, e.g., at the same time as one or more rounds of chemotherapy or radiotherapy, or a combination of both, are applied to a subject, and b) after the chemotherapy or radiotherapy, or a combination of both, is completed.

In another embodiment, the pharmaceutical compositions comprising HB-EGF and/or other agents are administered a) prior to one or more rounds of chemotherapy or radiotherapy, or a combination of both, and b) after the chemotherapy or radiotherapy, or a combination of both, is completed.

In another embodiment, the pharmaceutical compositions comprising HB-EGF and/or other agents are administered only after the chemotherapy or radiotherapy, or a combination of both, is completed.

Those of ordinary skill in the art will appreciate which conditions HB-EGF can effectively treat. The actual dose to be administered will vary depending upon the age, weight, and general condition of the subject as well as the severity of the condition being treated, the judgment of the health care professional, and composition or conjugate being administered. Therapeutically effective amounts can be determined by those skilled in the art, and will be adjusted to the particular requirements of each particular case. The amount of HB-EGF within a composition or conjugate administered will depend on the potency of the particular form of HB-EGF (e.g., mature HB-EGF or pro-HB-EGF), the magnitude of its effect on wound healing and epithelial regeneration, and the route of administration.

Compositions comprising HB-EGF, prepared as described herein (again, preferably provided as part of a pharmaceutical preparation), can be administered alone or in combination with one or more other therapeutically active agents for treating a wound in the context of radiotherapy-or-chemotherapy-associated oral mucositis, such as, but not limited to, analgesic agents, anesthetic agents, antibiotics, anti-inflammatory agents, substances that decrease neovascularization, substances that increase neoepithelial adherence, or other growth factors, or other agents that promote wound healing, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration multiple times a day, including, but not limited to, five times a day, four times a day, three times a day, twice daily, once daily, three times weekly, twice weekly, once weekly, twice monthly, once monthly, and any combination thereof. Preferred compositions are those requiring administration no more than once a day.

Compositions comprising HB-EGF can be administered prior to, concurrent with, or subsequent to other agents. If provided at the same time as other agents, HB-EGF can be provided in the same or in a different composition. Thus, HB-EGF and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising HB-EGF and a dose of a pharmaceutical composition comprising at least one other agent, such as another growth factor or drug for treating a wound inside the oral cavity, which in combination comprise a therapeutically effective dose, according to a particular dosing regimen. Similarly, HB-EGF and one or more other therapeutically active agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Kits

The invention also provides kits comprising one or more packaging, e.g., containers, holding mucoadhesive microgel compositions, e.g., as described above. The mucoadheisve microgel composition amy include any type of therapeutically active agent desired, e.g., as described above. In some instances, the kits include a HB-EGF loaded mucoadhesive microgel composition, and optionally one or more other drugs, e.g., for treating a given condition, such as wounds in the oral cavity and oropharynx before, during and/or after chemotherapy or radiotherapy, or a combination of both, such as, but not limited to, analgesic agents, anesthetic agents, antibiotics, anti-inflammatory agents, substances that decrease neovascularization, substances that increase neoepithelial adherence, or other growth factors, or other agents that promote wound healing. Containers can be formed from a variety of materials, including glass or plastic. A container may have a sterile access port (for example, the container may be an intravenous solution bag or a vial having a stopper pierceable by a hypodermic injection needle).

The kit can also comprise a package insert containing written instructions describing methods for care of a wound in the oral cavity or oropharyngeal wound due to radiotherapy-and-chemotherapy-associated oral mucositis as described herein. The package insert can be an unapproved draft package insert or can be a package insert approved by the Food and Drug Administration (FDA) or other regulatory body.

The following examples are offered by way of illustration and not by way of limitation.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

I. Mucoadhesive Microgel Fabrication

A. Synthesis of Dopamine-Acrylamide (DA)

Dopamine-acrylamide (DA) was synthesized and characterized following the procedure described by Patil et al. (N. Patil, C. Falentin-Daudré, C. Jérôme, C. Detrembleur, *Polym. Chem.*, 2015, 6, 2919-2933.) with some modifications. In brief, 31.6 mmol of $Na_2B_4O_7.10H_2O$ and 47.2 mmol of $Na_2CO_3$ were dissolved in 475 mL of "Milli-Q" grade water and the solution was degassed by nitrogen bubbling for 1 h. 15.8 mmol of dopamine hydrochloride were added under nitrogen atmosphere and the mixture was allowed to continue stirring for 30 minutes. Then, the solution was cooled at 0° C. and 63.2 mmol of acryloyl chloride were added drop-wise. In order to maintain the solution above pH 9, 84.9 mmol of $Na_2CO_3$ were added and the solution was stirred for 12 h at room temperature. After this, HCl was added to acidified solution pH to 1-2 and allowed to continue stirring for 1 h in an open vessel. The mixture was extracted 5 times with ethyl acetate and the brownish organic solution obtained from extraction was collected and dried over $Na_2SO_4$. Afterwards, the volume of the solution was reduced by rotary evaporation and DA was precipitated with hexane. The formed suspension was stored at fridge overnight to aid crystallization. Finally, the solid obtained by filtration of the suspension was dried in a vacuum oven overnight at room temperature. The synthesis is illustrated in FIG. 1A.

B. Synthesis of DA-Based Microgel

Figure 1B:
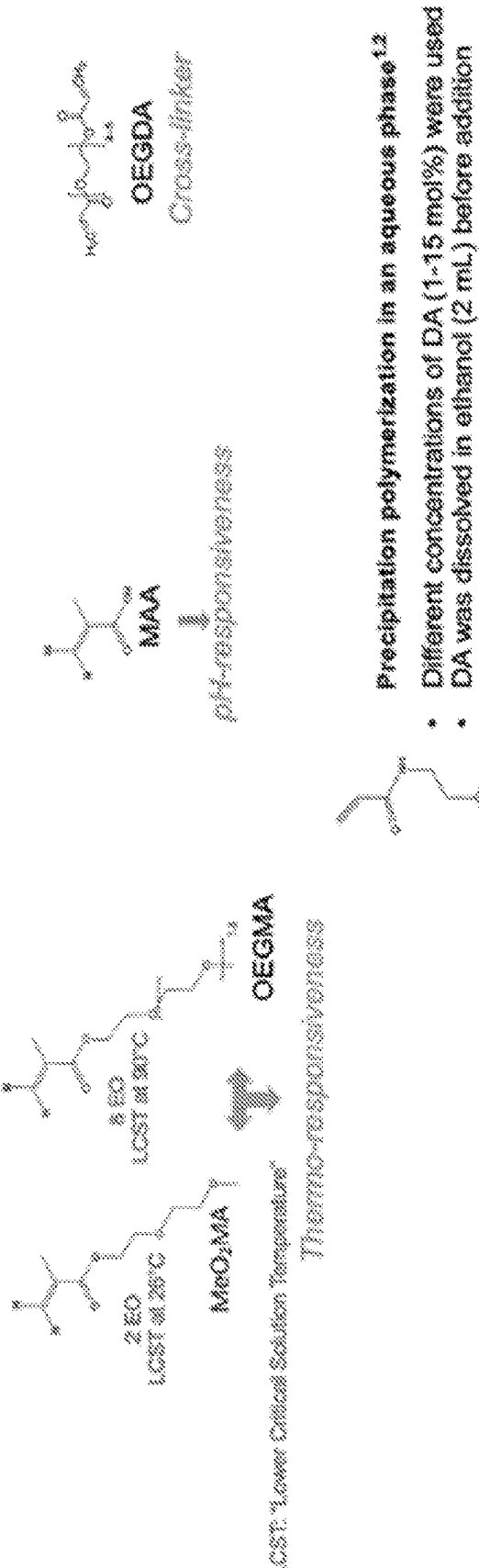
Figure 1C:
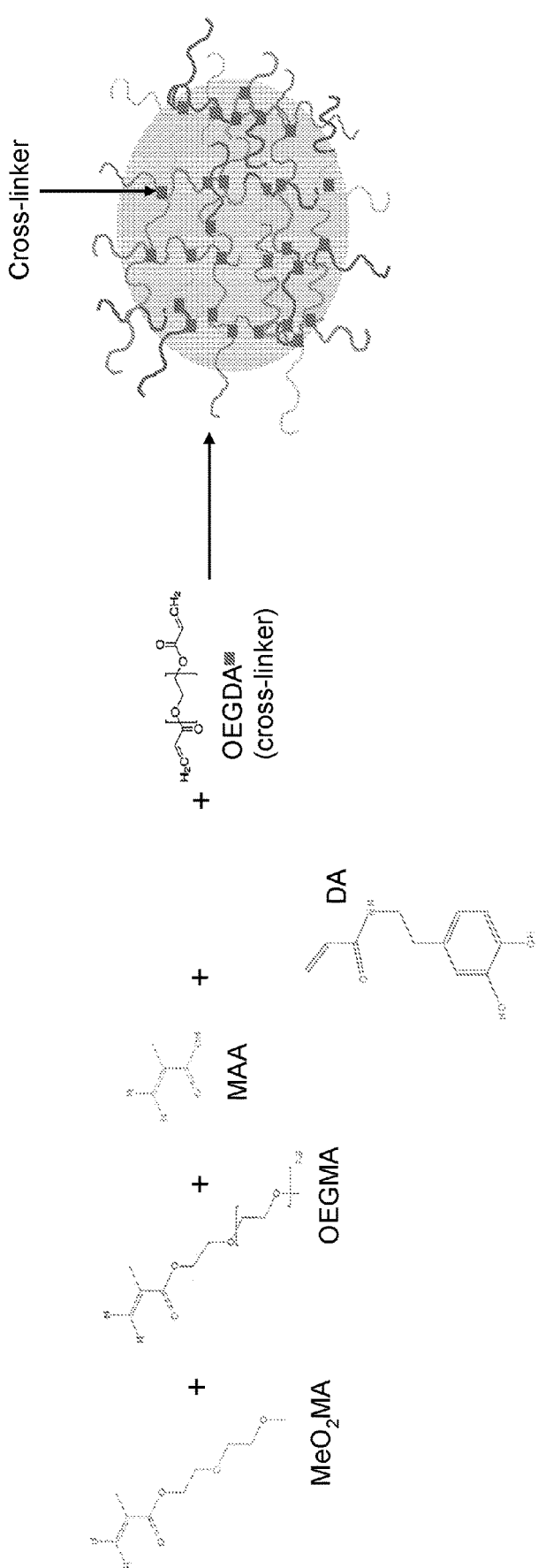

Microgels were synthesized by precipitation polymerization in a 250 mL 3-neck round-bottom flask. Briefly, 83.90 mmol of $MeO_2MA$ (di(ethylene glycol) methyl ether methacrylate), 0.573 mmol of $OEGMA_{7-8}$ (oligo(ethylene glycol) methyl ether methacrylate), 0.117 mmol of $OEGDA_{4-5}$ (poly(ethylene glycol) diacrylate) and 57.5 g of "Milli-Q" grade water were placed into a 250 mL 3-neck round-bottom flask. See FIG. 1B for structures and FIG. 10 for synthesis schematic. The reactor content was stirred at 150 rpm and purged with nitrogen for 45 min to remove oxygen at room temperature. Then, 0.305 mmol of MAA (methacrylic acid) dissolved in 2 mL of "Milli-Q" grade water and 3 mol % of DA dissolved in 2 mL of ethanol were added to the jacketed glass reactor and the mixture was heated up to 70° C. After adding the initiator (14.3 mg of potassium peroxydisulfate (KPS) dissolved in 2.5 mL of degassed water), the polymerization reaction was allowed to continue under nitrogen atmosphere while stirring for 6 h.

Then, the reaction mixture was subsequently cooled to 25° C. maintaining the stirring, and the final dispersion was purified by several centrifugation-redispersion cycles (10,000 rpm, 30 min) with "Milli-Q" grade water. After centrifugation, the supernatant was discarded to obtain the mucoadhesive microgel.

Figure 1D:
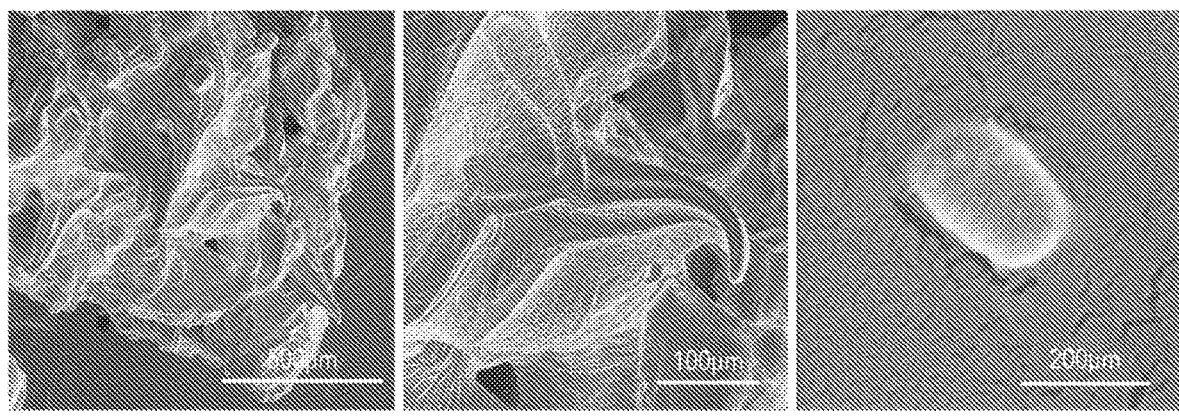
FIG. 1D provides scanning electron micrograph of a mucoadhesive microgel.

FIG. 1D provides scanning electron microscopy photos of the lyophylized mucoadhesive microgels prepared as described above. In FIG. 1D, left panel-red arrows show adhesive hooks of the material; middle panel-closeup un the hooks; right panel-hydrated hydrogels show rounded structures.

II. Production of HB-EGF Loaded Mucoadhesive Microgels

Figure 2A:
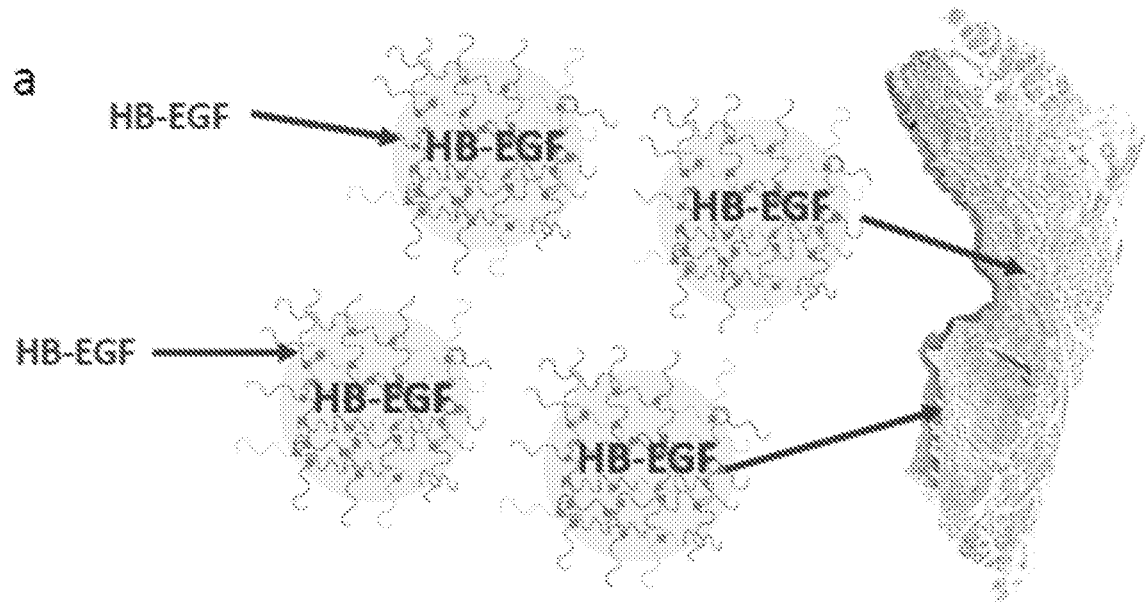
FIG. 2A provides a schematic illustration of a HB-EGF loaded mucoadhesive microgel in accordance with an embodiment of the invention.
Figure 2B:
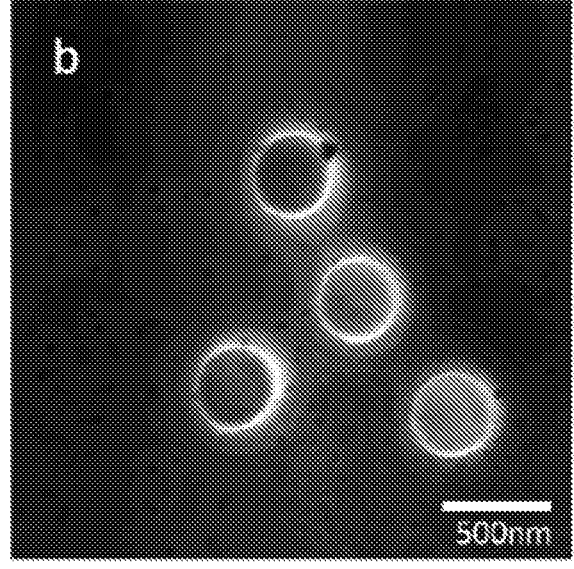
FIG. 2B provides an SEM image of a HB-EGF loaded mucoadhesive microgel in accordance with an embodiment of the invention.
Figure 2C:
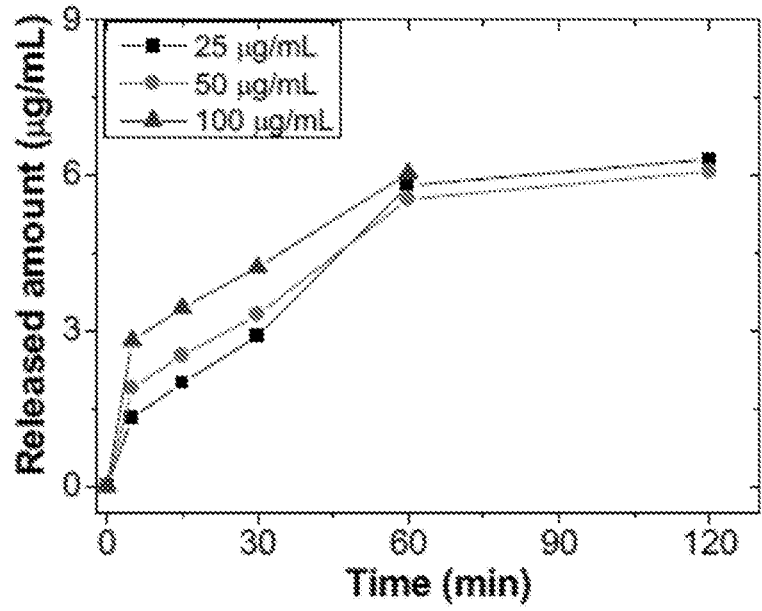
FIG. 2C provides a graph showing release data for the HB-EGF loaded mucoadhesive microgel shown in FIG. 2A.

Purified mucoadhesive microgels produced as described above were combined with 100 µg/ml of human HB-EGF. The resultant mixture was maintained for hours and enpsulation efficiency was observed to be 93%. A schematic of the resultant microgels is provided in FIG. 2A and an AFM image of the resultant microgels is shown in FIG. 2B. The resultant microgels were able to release 5 µg/ml of HB-EGF at 30 minutes as determined by mass spectrometry (See FIG. 2C).

III. Efficacy of HB-EGF Loaded Mucoadhesive Microgels

Figure 3:
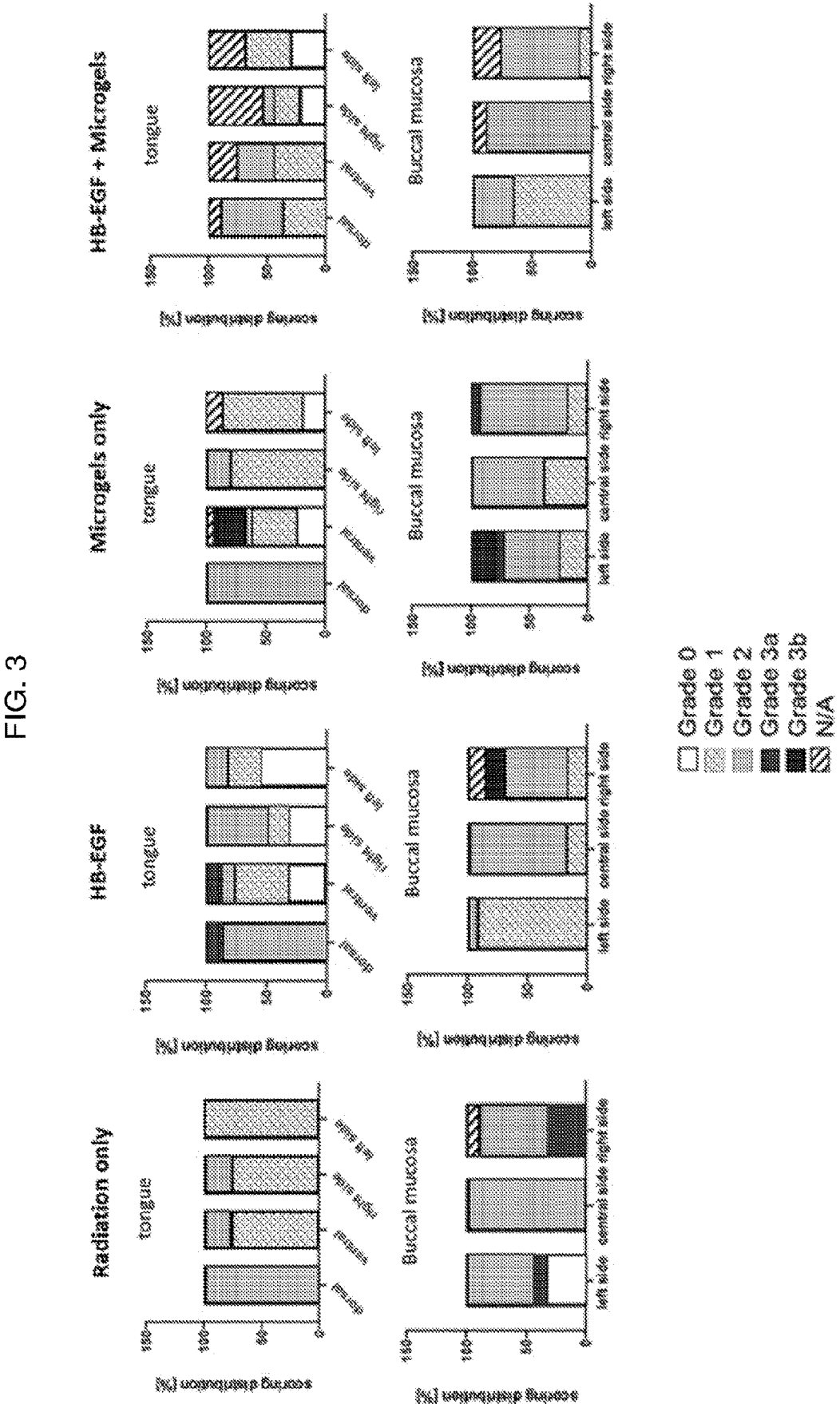
FIG. 3: HB-EGF with microgel delivery protects the oral cavity from radiation induced mucositis.
Figure 4:
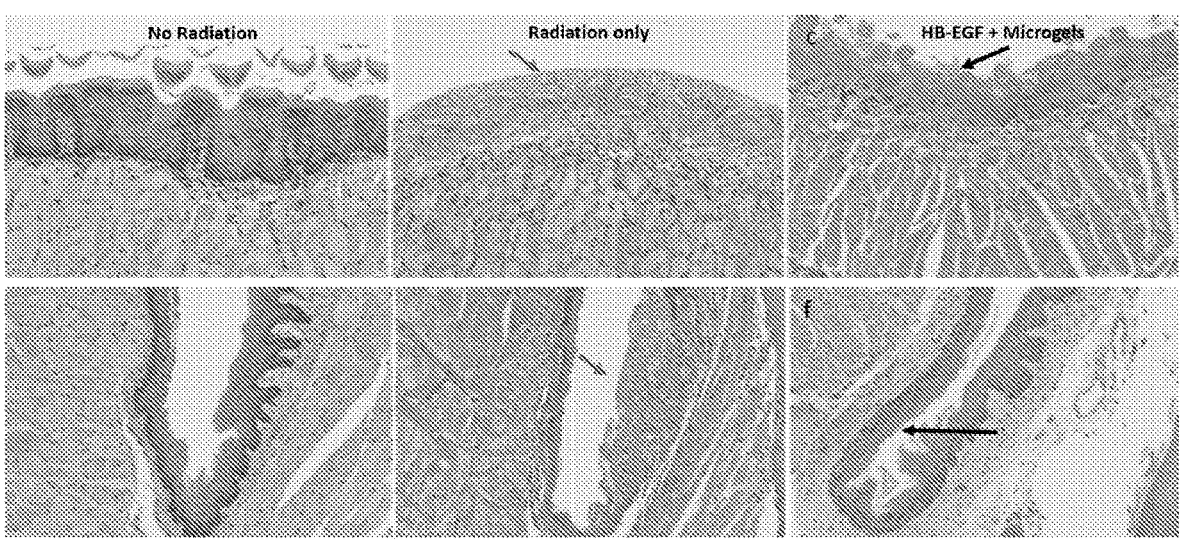
FIG. 4: HB-EGF with microgel delivery protects the oral cavity from radiation induced mucositis.

Studies were conducted showing that the HB-EGF loaded mucoadhesive microgel formulation produced in II above delivers in vivo, and that the formulation is effective in preventing radiation induced oral mucositis (See FIGS. 3 and 4).

As shown in FIG. 3, HB-EGF with microgel delivery prevents the severity radiation induced mucositis in the oral cavity. Blinded histopathological scoring (Sunavala-Dossabhoy G, Abreo F, Timiri Shanmugam P S, Caldito G. Histopathologic grading of oral mucositis. Oral Dis. 2015; 21(3):355-60) of the tongue (top row) and buccal mucosa (bottom row) at day 8 post radiation. ≥3 animals per condition, ≥3 slides per area. HB-EGF+microgels showed no cases of severe (grade 3 or above). n/a represents when the pathologist was unable to assess the slide due to artefact.

As shown in FIG. 4, dorsal tongue surface at day 9 post-radiation (top row) in the normal condition, radiation only without treatment and radiation treated with HB-EGF microgels. Radiation only shows a lack of epithelium with complete ulceration (red arrow). In the floor or the mouth (bottom row) mice treated with HB-EGF microgels show epithelial preservation (black arrow) compared to radiation only.

The HB-EGF microgels were the only treatment group that did not experience severe oral mucositis (grade 3 or higher). We also showed that our formulation by itself had benefit over the control, likely due to increased lubrication and also that our HB-EGF formulation combination had further benefit over the formulation alone. These results show we can deliver the drug to the target using our formulation with an excellent in vivo response.

V. Biodstribution

Figure 5:
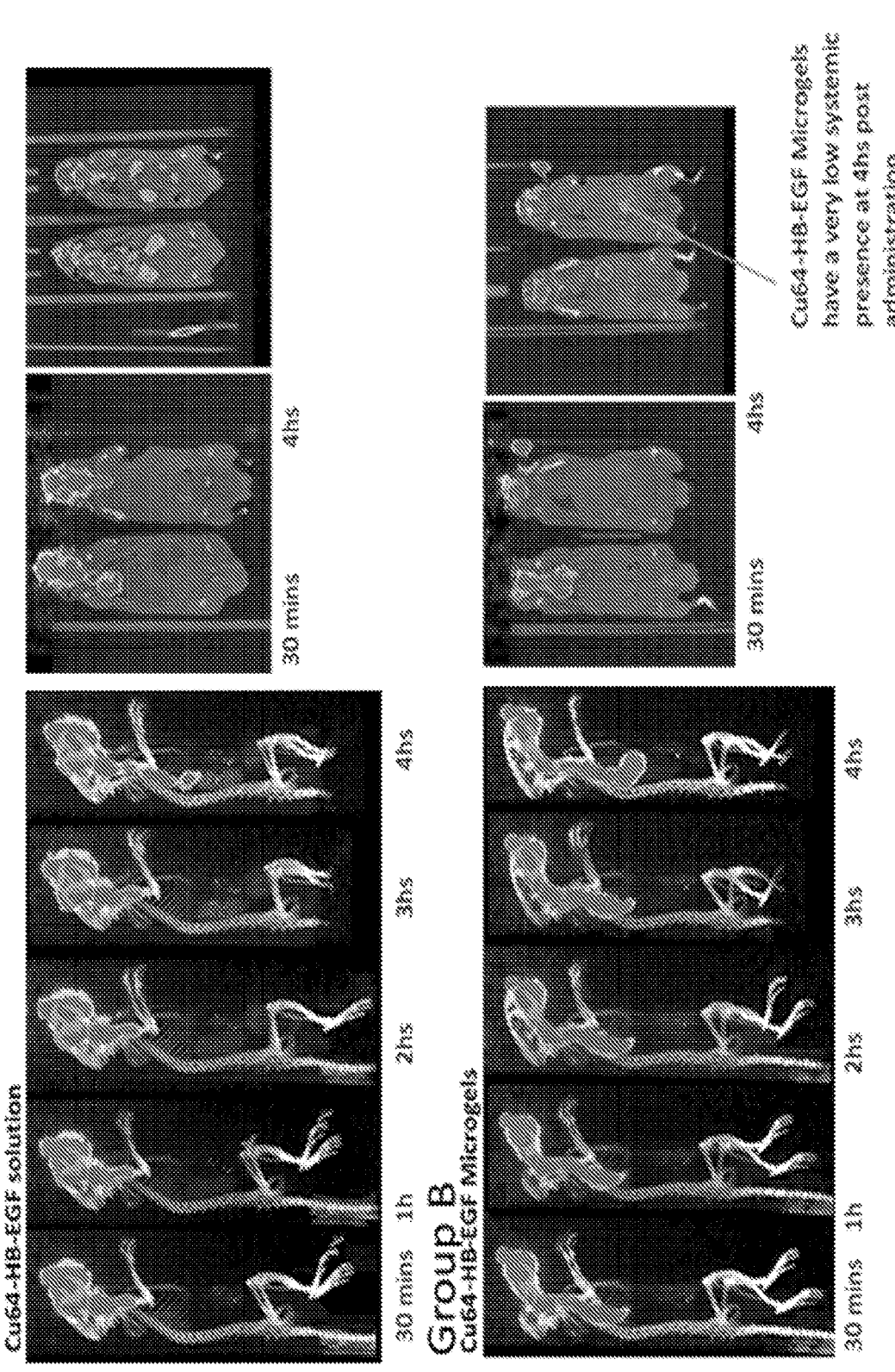
FIG. 5: Biodistribution study.

PET CT scans were performed and HB-EGF was labeled with Cu64 to evaluate biodistribution thereof. The results are shown in FIG. 5. Group A is the Cu64-HB-EGF solution, were only HB-EGF labeled with Cu64 was administered locally (mice mouth) in the form of a solution (sol). In Group B, the Cu64-HB-EGF was encapsulated in the mucoadhesive microgels and after 24 hs administered orally to the mice. Both groups underwent PET CT scans at 30 min, 1 hour, 2 hs, 3 hs and 4 hours. The Cu64 signal was measured by dividing the mice image's body into upper (U) and lower (L) regions of interest (ROI). If the signal comes from the upper ROI, it indicates that the compound was retained in the upper GI tract. If the signal comes from lower ROI it indicates that the compound is in the kidneys and bladder, indicating elimination. The absorption and elimination of group A is much faster as compared to group B that keeps the Cu64-HB-EGF in the oral cavity, avoiding systemic absorption proving the mucoadhesive properties of the microgel. Even al 4 hours the microgel encapsulated cu64-HB-EGF shows a very small amount in the lower ROI and strong signal from the upper ROI indicating high retention and low elimination of the labeled product.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A mucoadhesive microgel therapeutically active agent composition comprising a therapeutically active agent loaded into a mucoadhesive cross-linked microgel comprising a crosslinked poly(ethylene glycol) methyl ether methacrylate polymer comprising a mucoadhesive functionality, wherein the crosslinked poly(ethylene glycol) methyl ether methacrylate polymer consists of diethylene glycol methacrylate monomeric units, oligoethylene glycol methacrylate monomeric units, methacrylic acid monomeric units, dopamine acrylamide monomeric units, and crosslink moieties, wherein the therapeutically active agent is heparin binding epidermal growth factor (HB-EGF), wherein the mucoadhesive microgel is suitable for treating radiotherapy or chemotherapy-induced oral mucositis, and wherein the crosslink moieties are selected from the group consisting of oligo(ethylene glycol) diacrylate comprising from 1 to 10 ethylene glycol units, poly(propylene glycol) diacrylate, ethylene glycol dimethacrylate, glycerol dimethacrylate, N,N'-methylenebisacrylamide, N,N-(1,2-dihydroxyethylene) bisacrylamide, poly(ethylene glycol)diacrylamide, bis(2-methacryloyl)oxyethyl disulfide and N,N-bis(acryloyl) cystamine, and crosslink moieties having di(meth)acrylate end groups and a moiety selected in the group consisting of $-(CH_2-CH_2-O)_n-CH_2-CH_2-$ where n is from 0 to 6, $-NH-CH_2-NH-$ and mixtures thereof.

2. The mucoadhesive microgel therapeutically active agent composition according to claim 1, wherein the oligoethylene glycol methacrylate monomeric units comprise from 6 to 10 ethylene glycol moieties.

3. The mucoadhesive microgel therapeutically active agent composition according to claim 1, wherein the composition further comprises one or more additional mucoadhesive agents.

4. The mucoadhesive microgel therapeutically active agent composition according to claim 3, wherein the one or more additional mucoadhesive agents are mucoadhesive polymeric agents.

5. The mucoadhesive microgel therapeutically active agent composition according to claim 4, wherein the one or more additional mucoadhesive agents are mucoadhesive polymeric agents selected from the group consisting of naturally occurring mucoadhesive polymeric agents, synthetic mucoadhesive polymeric agents and combinations thereof.

6. The mucoadhesive microgel therapeutically active agent composition according to claim 5, wherein the naturally occurring mucoadhesive polymeric agents are polysaccharides.

7. The mucoadhesive microgel therapeutically active agent composition according to claim 6, wherein the polysaccharides are selected from the group consisting of starches, chitosan, heparin and combinations thereof.

8. The mucoadhesive microgel therapeutically active agent composition according to claim 5, wherein the synthetic mucoadhesive polymeric agent is a poloxamer.

9. The mucoadhesive microgel therapeutically active agent composition according to claim 1, wherein the composition is in the form of an aqueous dispersion of microgel particles or in the form of a film comprising microgel particles.

10. A method of treating oral mucositis in a subject, the method comprising:

orally administering to the subject the mucoadhesive microgel therapeutically active agent composition according to claim 1.

11. A method of preparing the mucoadhesive microgel therapeutically active agent composition according to claim 1, the method comprising:

preparing a mucoadhesive microgel via a precipitation polymerization method comprising contacting in an aqueous phase, in the presence of a cross-linking agent, diethylene glycol methacrylate monomeric units, oligoethylene glycol methacrylate monomeric units, methacrylic acid monomeric units, and dopamine acrylamide monomeric units, at a temperature between 40° C. and 90° C., initiating polymerization by adding an initiator to form a polymerization reaction mixture, cooling the polymerization reaction mixture, and obtaining a mucoadhesive cross-linked microgel; and loading the mucoadhesive cross-linked microgel with a therapeutically active agent.

12. A kit comprising:

a dosage of the mucoadhesive microgel therapeutically active agent composition according to claim 1; and a packaging.

13. The mucoadhesive microgel therapeutically active agent composition according to claim 1, wherein entrapment efficiency of the HB-EGF is higher than 90%.

14. The mucoadhesive microgel therapeutically active agent composition according to claim 1, wherein the mucoadhesive microgel therapeutically active agent composition provides for continuous release of HB-EGF for 6 hours or longer.

15. The mucoadhesive microgel therapeutically active agent composition according to claim 1, wherein the crosslinked polyethylene glycol methyl ether methacrylate polymer consists of diethylene glycol methyl ether methacrylate, oligoethylene glycol methyl ether methacrylate, polyethylene glycol diacrylate, methacrylic acid, and dopamineacrylamide.

* * * * *